United States Patent [19]

Thompson

[11] Patent Number: 4,483,206

[45] Date of Patent: Nov. 20, 1984

[54] REACTOR CATALYST REMOVAL VALVE

[75] Inventor: Timothy J. Thompson, Detroit, Mich.

[73] Assignee: Marathon Oil Company, Findlay, Ohio

[21] Appl. No.: 443,408

[22] Filed: Nov. 22, 1982

[51] Int. Cl.$^3$ ............................ G01N 1/10; F16K 1/20
[52] U.S. Cl. ................................. 73/863.85; 137/244; 251/300; 422/219; 422/310
[58] Field of Search ........................ 422/219, 232, 310; 251/300, 301, 302; 73/864.63, 864.64, 864.65, 863.85; 137/614.01, 244; 414/292; 436/37

[56] References Cited

U.S. PATENT DOCUMENTS

| Re. 105 | 1/1848 | Lincoln | 251/300 |
|---|---|---|---|
| 73,822 | 1/1868 | Marchbank | 251/300 |
| 455,733 | 7/1891 | Bell | 73/864.65 |
| 533,175 | 1/1895 | Krouse | 73/864.65 |
| 600,444 | 3/1898 | Perkins | 137/614.01 |
| 606,025 | 6/1898 | Perry | 251/300 |
| 693,781 | 2/1902 | Brown | 137/614.01 X |
| 867,303 | 10/1907 | Robertson | 251/300 |
| 1,327,351 | 1/1920 | Norton | 251/300 X |
| 1,480,141 | 1/1924 | Artese | 251/300 |
| 1,938,224 | 12/1933 | Remington et al. | 73/864.65 |
| 2,174,100 | 9/1939 | Walker | 73/864.65 |
| 3,045,706 | 7/1962 | Dillon | 251/301 X |
| 3,521,665 | 7/1970 | Poulsen | 137/383 |

Primary Examiner—Barry S. Richman
Assistant Examiner—Brion P. Heaney
Attorney, Agent, or Firm—Jack L. Hummel; Rodney F. Brown

[57] ABSTRACT

A pivotal valve (10) for use in removal of catalysts (40) from reactors (30) having outer and inner flange plates (110, 120) with a plurality of spacers (130, 132, 134) firmly attached therebetween to form open regions (300, 302) between the spacers and the flange plates to allow free passage of the catalyst material (40) upon closure of the valve (10) to prevent jamming of the valve (10), a gate (140) pivotally attached between the plates (110, 120) for selectively opening and closing the nozzle hole (25) on the reactor nozzle (20) and an arcuate steel plate (190) on the pivotal gate (140) for selectively engaging the inner flange plate (120) next to the nozzle (20) to provide a complete circular seal around the nozzle hole (25) when the circular gate (140) is in the closed position.

4 Claims, 5 Drawing Figures

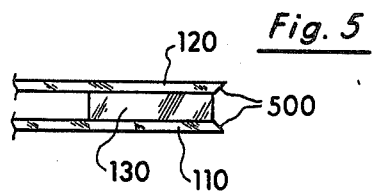
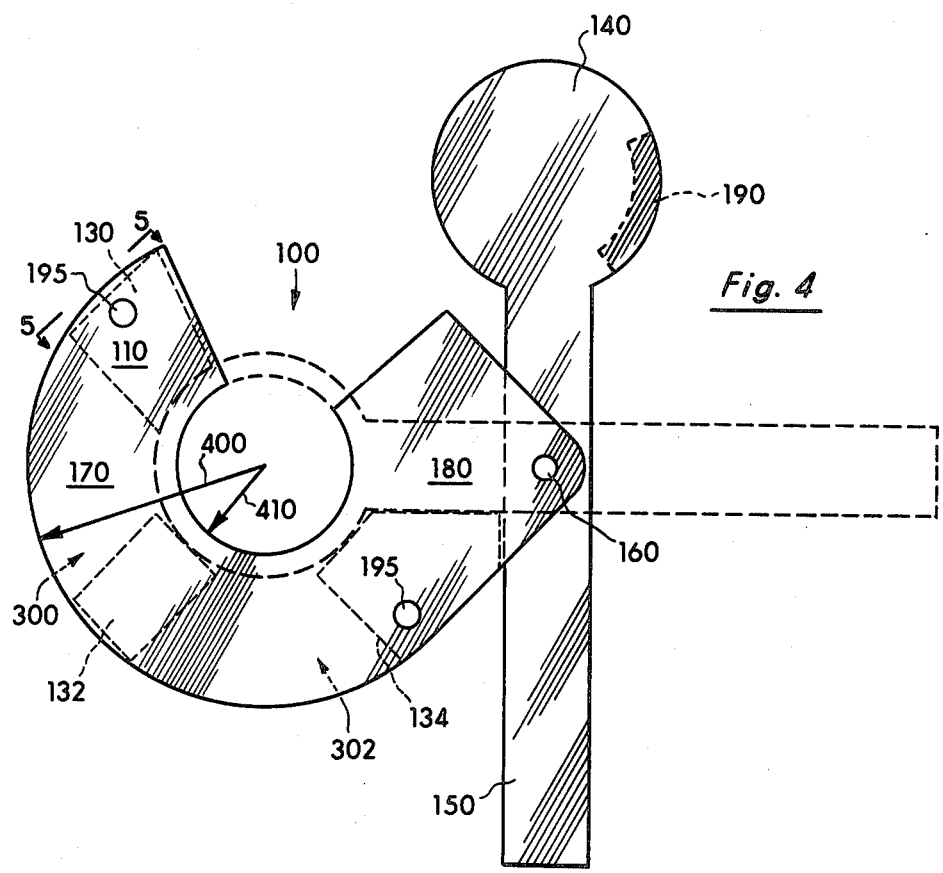

REACTOR CATALYST REMOVAL VALVE

FIELD OF THE INVENTION

The present invention relates to a pivotal valve and, more particularly, to a pivotal valve having formed open regions therein for removal of material to prevent jamming of the valve and an arcuate segmented portion on the pivotal valve to provide a full and complete seal.

BACKGROUND ART

In reactors containing a large amount of catalyst, it becomes necessary to remove the catalyst from the reactor upon degradation of the catalyst. Sampling tubes are sometimes inserted into the reactor to sense the degradation or performance level of the catalyst material. In such environments, the commonly used slide valve is rendered inoperable due to the presence of the sampling tube extending from the reactor nozzle. It becomes necessary to provide a valve which can be selectively installed to the reactor nozzle prior to when the sampling tube is to be removed. After installation of the valve, the sampling tube can be removed and the valve closed to prevent loss of the catalyst material.

A patentability search was conducted on the invention and the following patents were uncovered:

| INVENTOR | U.S. PAT. NO. | DATE |
| --- | --- | --- |
| Levi Lincoln | RE 105 | Jan. 25, 1848 |
| John Marchbank | 73,822 | Jan. 28, 1868 |
| N. W. Krouse | 533,175 | Jan. 29, 1895 |
| J. T. Perkins | 600,444 | March 8, 1898 |
| J. C. Perry | 606,025 | June 21, 1898 |
| W. S. Robertson | 867,303 | October 1, 1907 |
| J. Artese | 1,480,141 | Jan. 8, 1924 |
| B. F. Remington | 1,938,224 | Dec. 5, 1933 |
| W. L. Walker | 2,174,100 | Sept. 26, 1939 |
| R. D. Poulsen | 3,521,665 | July 28, 1970 |

The 1898 patent issued to Perry for a water faucet valve includes a pivotal plate for selectively engaging enveloping flanges to open and close a passageway carrying water.

The 1868 patent issued to Marchbank sets forth a pivotal valve having an extending handle thereon for selectively opening and closing the gate through a transverse bar. The 1848 patent issued to Lincoln also sets forth a pivotal gate having an extended handle disposed between two plates.

The 1907 patent issued to Robertson shows a gate being pivoted at one end and having a pre-formed circular gate with an outwardly extending handle at the other end. The 1970 patent issued to Poulsen discloses a gate valve circular in shape for use in irrigation systems and the 1939 patent issued to Walker sets forth an oil sampler utilizing a pivotal gate.

The 1924 patent issued to Artese discloses a pivotal gate having the pivot in the middle with an extending handle portion. The Artese pivotal gate is utilized for water distribution and regulation thereof. The 1933 patent issued to Remington et al also utilizes a pivotal gate to obtain a water sample. The 1898 patent issued to Perkins shows a pipe coupling utilizing a pivotal gate for selectively opening and closing a passageway. Finally, the 1895 patent issued to Krouse also shows a pivotal valve for selectively closing an opening.

However, none of the prior art references set forth the pivotal retrofittable valve of the present invention having formed open regions for removal of any material carried in the passageway which could clog or jam the valve and having an arcuate segmented portion on the pivotal valve to provide a full and complete seal around the passageway as presented in the next section.

DISCLOSURE OF THE INVENTION

The problem faced in designing a reactor catalyst removal valve is to produce a design that is retrofittable to a reactor nozzle which may have a sampling pipe extending therefrom and which will also close in the presence of reactor catalyst material without jamming to provide a complete seal.

The pivotal valve of the present invention is capable of selective attachment to the reactor nozzle having a sampling pipe extending therefrom and includes outer and inner flange plates which are spaced apart from each other by means of a plurality of spacers so that open regions are formed between the spacers and the plates to provide free-flow of any catalyst material trapped in the pivotal valve upon closure to prevent clogging or jamming. A circular gate is pivotally attached between the plates having an extending handle for selective opening and closing of the valve over the reactor nozzle. On one edge of the circular gate an arcuate steel plate is attached for engaging the inner flange plate next to the reactor nozzle in order to provide a complete circular seal around the nozzle hole when the circular gate is in the closed position.

DESCRIPTION OF THE DRAWINGS

FIG. 4 is an outside planar view showing the various components of the valve of the present invention.

FIG. 5 is a partial side view showing the beveled edges and spacers of the present invention.

BEST MODE FOR CARRYING OUT THE INVENTION

Figure 1:
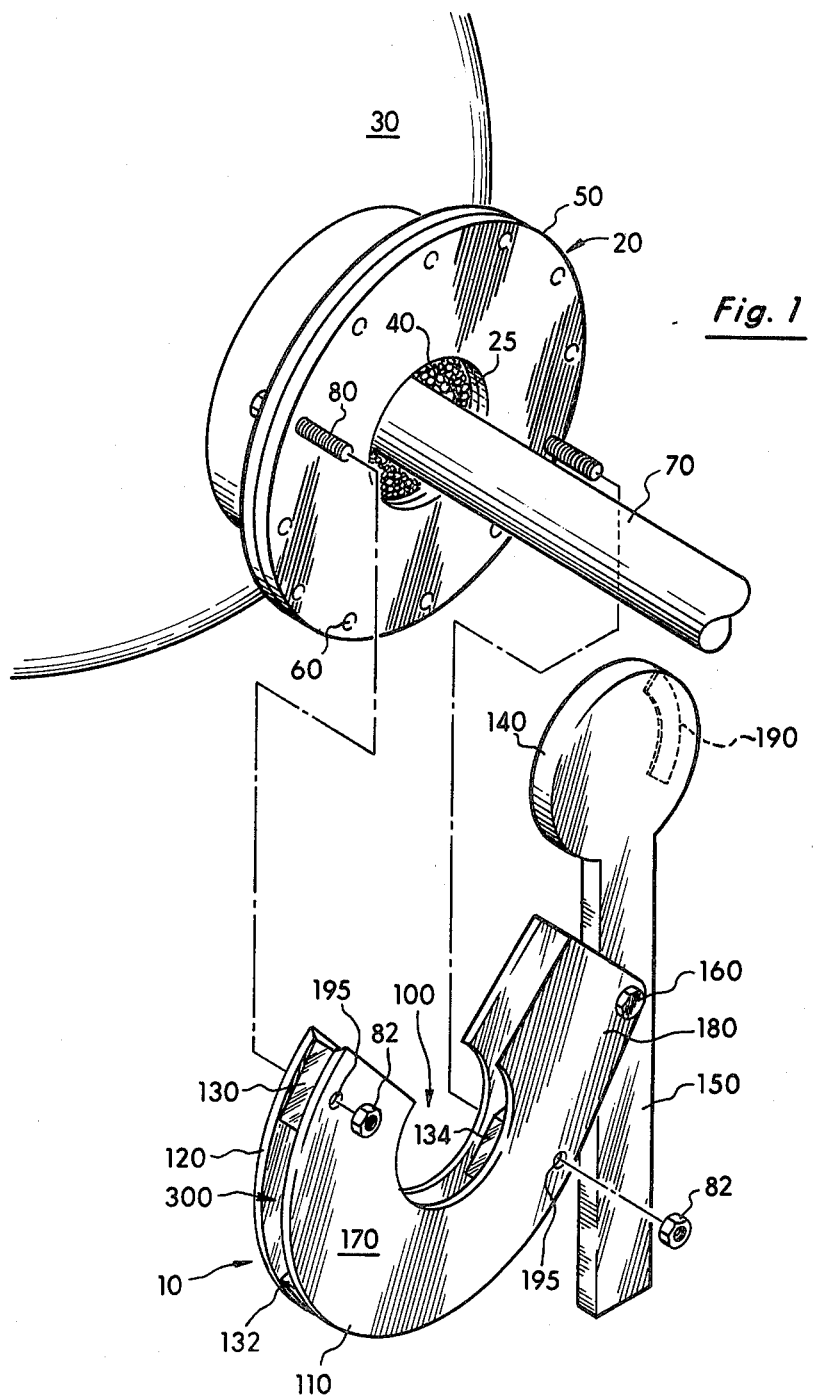
FIG. 1 sets forth in perspective view, the pivotal gate (10) of the present invention being mounted to a typical reactor nozzle having a sampling pipe extending therefrom.

In FIG. 1, the pivotal valve (10) of the present invention is set forth in relationship to the nozzle (20) and nozzle hole (25) of a reactor or container (30) containing a large amount of catalyst material (40). The nozzle (20) generally comprises a circular flange (50) having a plurality of holes (60) formed there around. A sampling pipe (70) extends from the passageway of the reactor nozzle and may be utilized to ascertain the integrity and performance of the catalyst material (40). The reactor (30) is a large vertical cylinder having a hemispherical shaped bottom.

In operation and as shown in FIG. 1, the valve (10) of the present invention can be selectively installed to the reactor nozzle (20) by inserting mounting bolts (80) and nuts (82) into opposing holes (60) and then by inserting the pivotal valve (10) of the present invention in such a fashion that the opened-C area (100) is mounted over the sampling pipe (70). The pivotal valve (10) of the present invention includes an outer flange plate (110), an inner flange plate (120) identical in configuration to the outer plate (110), a series of spacers (130, 132 and 134), and a circular gate (140) with an extending handle (150) pivotally attached between the outer plate (110) and the inner plate (120) by means of a pivot (160). Each of the outer and inner plates (110, 120) has a first substantially annular area (170) and a second area (180) where the pivoting of the circular gate (140) occurs. Attached to the circular gate (140) is an arcuate seal plate (190) whose purpose will be more fully described subsequently.

As shown in FIG. 1, the pivotal valve (10) of the present invention is mounted to the nozzle (20) of the reactor (30) by means of bolts (80) and nuts (82) through formed holes (60). The valve of the present invention is designed to be selectively removed and attached to the reactor nozzle without interfering with the operation of the sampling pipe (70).

Figure 2:
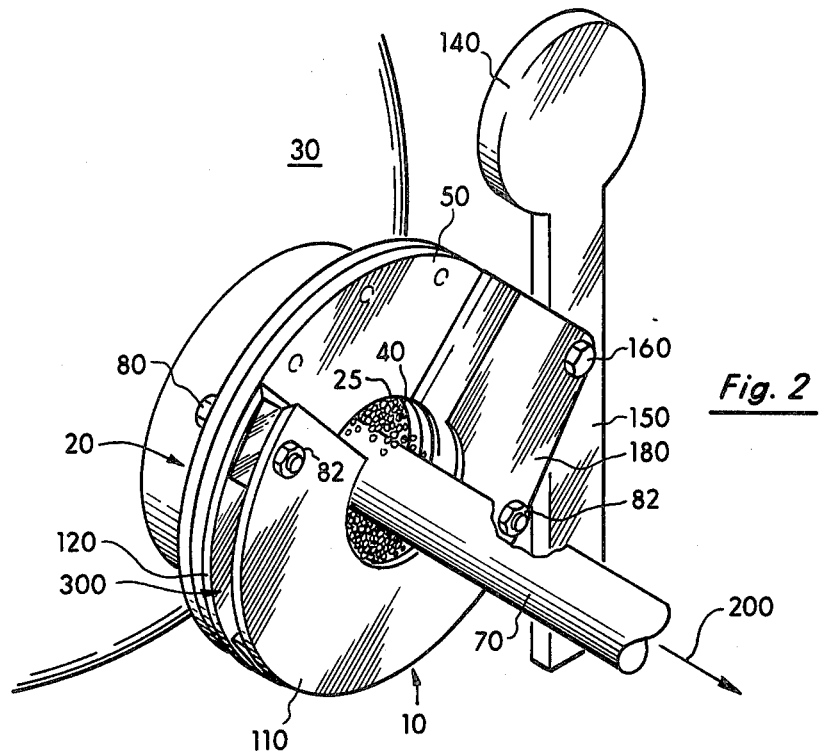
FIG. 2 sets forth the pivotal valve of FIG. 1 after being mounted to the reactor nozzle around the sampling pipe with the valve in the fully opened position.
Figure 3:
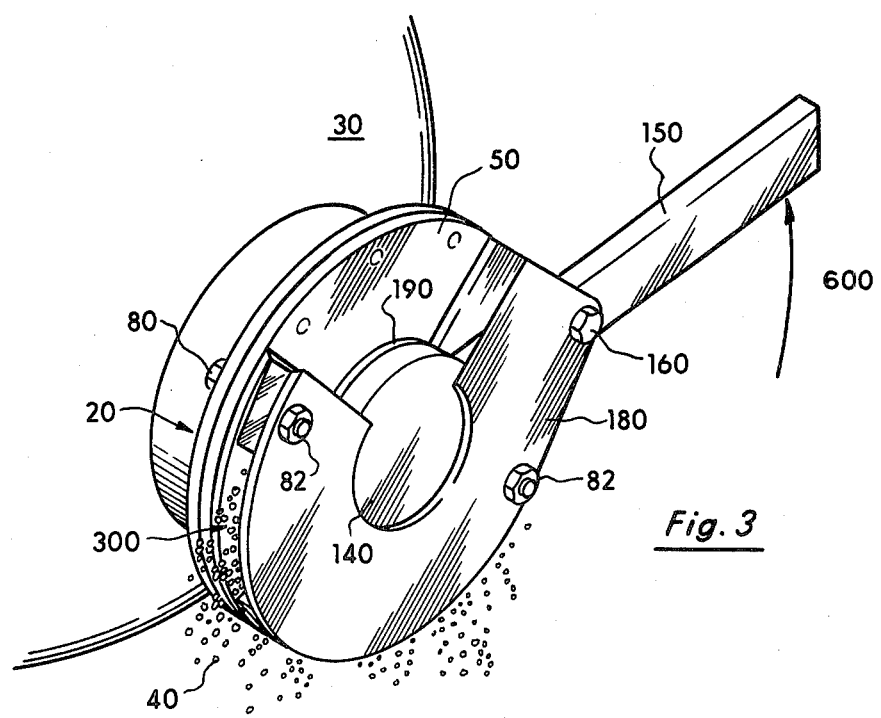
FIG. 3 shows the reactor valve of FIG. 2, after removal of the sampling pipe, in the fully closed position and the free-flow or release of catalyst material from around the valve to prevent jamming.

In FIG. 2, the pivotal valve (10) of the present invention is shown mounted to the reactor nozzle. The sampling pipe (70) can then be removed in the direction of arrow (200). In doing so some of the catalyst material (40) is dropped out of the reactor (30). As soon as the sampling pipe (70) is fully removed from the reactor (30), the handle (150) is moved quickly in the direction of arrow (600), as shown in FIG. 3, to fully close the pivotal valve (10) of the present invention. Because some catalyst material may exist from the reactor (30), pathways must be provided for the catalyst material to exit from the valve (10) in order to prevent jamming or non-closure of the valve. Hence, under the teachings of the present invention, formed open regions (300) are provided between the spacers (130, 132 and 134) and the outer and inner flange plates (110, 120) as shown in FIG. 3 to allow the catalyst material (40) to freely exit without jamming the pivotal gate (140).

In FIG. 4, the details of the pivotal gate (10) of the present invention are shown. The view in FIG. 4 is the view of the outer side of the valve away from the reactor (30) as the valve (10) approaches for installation. The outer flange plate (110) is shown having a first substantially annular area (170) with an outer diameter (400) corresponding to the outer diameter of the nozzle (20) of the reactor (30) and an inner diameter (410) corresponding to the diameter of the nozzle hole (25). The outer flange plate (110) has a second area (180) having an outer portion extending beyond the outer diameter (400) to encompass the pivot pin (160) and an inner portion continuing and corresponding to the diameter (410) of the nozzle hole (25). In the preferred embodiment, the outer and inner flange plates (110 and 120) are identical and are preferably made of one-quarter inch thick steel plate shaped as shown in FIG. 4 and discussed above. Each substantially annular plate forms a substantially opened-C opening in the direction of arrow (100) wherein the opening (100) is greater than the diameter of the sampling pipe (70). In this fashion the valve (10) can be placed around the sampling pipe (70) or other plumbing or devices for installation to the reactor nozzle (20).

A plurality of spacers (130, 132 and 134) are provided between the outer and inner flange plates (110 and 120) to hold the plates a predetermined distance apart which, in the preferred embodiment, is nine/thirty seconds of an inch. The spacers (130, 132, 134) are of the configuration and shape shown in FIG. 4. Most importantly, the spacers (130, 132 and 134) are spaced a predetermined distance apart from each other as indicated by open regions (300 and 302). As priorly discussed, this permits the free-flow of catalyst material (40) out from around the area of the valve to prevent jamming or clogging of the gate (140) when closing.

The circular gate (140) is pivotally attached to plates (110 and 120) at pivot (160) and is capable of selectively opening and closing the nozzle hole (25). As shown in FIG. 4, the gate (140) is in the full open position. However, as indicated by the dotted line, the gate can fully close against the outer and inner flange plates (110 and 120) to effectuate a seal over the nozzle hole (25). In the preferred embodiment, the circular gate (140) is slightly larger than the nozzle hole (25) which, for example, can be four inches in diameter. The length of the handle (150) with the pivot located between the handle and the circular gate, in the preferred embodiment, is between six to eight inches. The circular gate and handle is integral and is also made from one-quarter inch thick steel.

An arcuate seal plate (190) is provided on the inner side of the circular gate as shown by the dotted lines in FIG. 4 so that when the circular gate (140) is in the fully closed position as shown by the dotted lines, the arcuate seal plate (190) completes the circular seal around the nozzle hole (25) to prevent any leakage of the catalyst material (40) from the nozzle hole (25). As mentioned, the inner plate (120) is one-quarter inch thick and if the arcuate seal plate (190) were not provided, leakage through the opened-C portion (100) of the valve (10) of the catalyst material would occur. By providing the arcuate seal plate (190), no such leakage occurs.

FIG. 5 sets forth the beveled edges (500) of the flange plates (110 and 120) at the location where the pivotal gate (140) enters between the flange plates. The beveled edges (500) are provided to insure ease of gate engagement with the plates.

The valve of the present invention has been specifically set forth in the above disclosure, but it is to be understood that modifications and variations can be made to the design which would still fall within the scope and coverage of the appended claims herewith.

I claim:

1. A pivotal valve (10) for selective attachment to a nozzle (20) of a container (30) having a pipe (70) installed through a nozzle hole (25) of said nozzle (20) into solid particulate material (40) found in the container (30), said pivotal valve (10) comprising:

outer and inner flange plates (110, 120), each of said flange plates having a first substantially annular area (170) with an outer diameter (400) corresponding to the outer diameter of a nozzle and an inner diameter (410) corresponding to the diameter of a nozzle hole and a second area (180) having an outer portion extending beyond said outer diameter and an inner portion continuing and corresponding to the diameter of a nozzle hole, said first and second areas (170, 180) forming a substantially opened-C area (100) having an opening greater than the diameter of a pipe (70), a plurality of spacers (130, 132, 134) firmly attached between outer and inner flange plates (110, 120) to hold said plates a predetermined distance apart and to provide formed open regions (300, 302) between said spacers (130, 132, 134), said open regions (300, 302) being large enough to permit the passage of solid particulate material, a circular gate (140) with an outwardly extending handle (150) pivotally attached between said plates (110, 120) for selectively opening and closing a nozzle hole when said plates (110, 120) are mounted to a nozzle, and means (80, 82) for selectively attaching said plates (110, 120) to a nozzle.

2. The pivotal valve (10) of claim 1 further comprising:
an arcuate steel plate (190) on said gate (140) for engaging the inner plate (120) next to a nozzle to provide a complete circular seal around a nozzle hole when said circular gate is in said closed position.

3. A pivotal valve (10) for use in removal of solid catalyst particles (40) from the interior of a catalytic reactor (30), said reactor (30) having a nozzle (20) providing communication between the interior and exterior of said reactor via a nozzle hole (25) and said valve (10) being capable of selective attachment to the reactor nozzle (20) when a sampling pipe (70) is installed through the nozzle hole (25), said pivotal valve (10) comprising:
outer and inner flange plates (110, 120), each of said flange plates having a first substantially annular area (170) with an outer diameter (400) corresponding to the outer diameter of a nozzle and an inner diameter (410) corresponding to the diameter of a nozzle hole and a second area (180) having an outer portion extending beyond said outer diameter and an inner portion continuing and corresponding to the diameter of a nozzle hole, said first and second areas (170, 180) forming a substantially opened-C area (100) having an opening greater than the diameter of a sampling pipe which can be installed therethrough,
a plurality of spacers (130, 132, 134) firmly attached between said outer and inner flange plates (110, 120) to hold said plates a predetermined distance apart and to provide formed open regions (300, 302) between said spacers (130, 132, 134), said open regions (300, 302) being large enough to permit the passage of catalyst particles,
a circular gate (140) with an outwardly extending handle (150) pivotally attached between said plates (110, 120) for selectively opening and closing a nozzle hole when said plates (110, 120) are mounted to a nozzle, and
means (80, 82) for selectively attaching said plates (110, 120) to a nozzle.

4. A pivotal valve (10) for use in removal of solid catalyst particles (40) from the interior of a catalytic reactor (30), said reactor (30) having a nozzle (20) providing communication between the interior and exterior of said reactor via a nozzle hole (25) and said valve (10) being capable of selective attachment to the reactor nozzle (20) when a sampling pipe (70) is installed through the nozzle hole (25), said pivotal valve (10) comprising:
outer and inner flange plates (110, 120), each of said flange plates having a first substantially annular area (170) with an outer diameter (400) corresponding to the outer diameter of a nozzle and an inner diameter (410) corresponding to the diameter of a nozzle hole and a second area (180) having an outer portion extending beyond said outer diameter and an inner portion continuing and corresponding to the diameter of a nozzle hole, said first and second areas (170, 180) forming a substantially opened-C area (100) having an opening greater than the diameter of a sampling pipe which can be installed therethrough,
a plurality of spacers (130, 132, 134) firmly attached between said outer and inner flange plates (110, 120) to hold said plates a predetermined distance apart and to provide formed open regions (300, 302) between said spacers (130, 132, 134), said open regions (300, 302) being large enough to permit the passage of catalyst particles,
a circular gate (140) with an outwardly extending handle (150) pivotally attached between said plates (110, 120) for selectively opening and closing a nozzle hole when said plates (110, 120) are mounted to a nozzle,
an arcuate seal plate (190) on said gate (140) for engaging the inner plate (120) next to a nozzle to provide a complete circular seal around a nozzle hole when said circular gate (140) is in said closed position, and
means (80, 82) for selectively attaching said plates (110, 120) to a nozzle.

* * * * *